United States Patent
Loosemore

(10) Patent No.: US 9,913,859 B1
(45) Date of Patent: Mar. 13, 2018

(54) DAIRY ANIMAL TEAT DISINFECTANT

(71) Applicant: Webco Chemical Corporation, Dudley, MA (US)

(72) Inventor: Michael J. Loosemore, Dudley, MA (US)

(73) Assignee: Webco Chemical Corporation, Dudley, MA (US)

( * ) Notice: Subject to any disclaimer, the term of this patent is extended or adjusted under 35 U.S.C. 154(b) by 0 days.

(21) Appl. No.: 13/842,354

(22) Filed: Mar. 15, 2013

(51) Int. Cl.
*A61K 33/36* (2006.01)
*A01N 25/00* (2006.01)
*A61K 31/155* (2006.01)
*A61K 33/18* (2006.01)

(52) U.S. Cl.
CPC ............ *A61K 33/18* (2013.01); *A61K 31/155* (2013.01)

(58) Field of Classification Search
None
See application file for complete search history.

(56) References Cited

U.S. PATENT DOCUMENTS

| | | | |
|---|---|---|---|
| 3,950,554 A | 4/1976 | Prince | |
| 4,399,353 A | 8/1983 | Adkins et al. | |
| 4,668,692 A | 5/1987 | Noorlander et al. | |
| 4,670,263 A | 6/1987 | Noorlander | |
| 5,211,961 A | 5/1993 | Adkinson | |
| 5,370,875 A | 12/1994 | Rogozinski | |
| 5,399,353 A | 3/1995 | Bartnik et al. | |
| 5,618,841 A * | 4/1997 | Kross | A01N 59/12 514/557 |
| 5,641,498 A | 6/1997 | Loosemore | |
| 5,942,239 A | 8/1999 | Huprich et al. | |
| 6,037,386 A | 3/2000 | Modak et al. | |
| 6,107,344 A | 8/2000 | Loosemore | |
| 6,183,785 B1 | 2/2001 | Westfall | |
| 6,203,812 B1 * | 3/2001 | Ehrhard | A01N 25/24 424/405 |
| 6,395,289 B1 * | 5/2002 | Ehrhard | A01N 25/24 424/401 |
| 6,440,442 B1 * | 8/2002 | Ehrhard | A01N 25/24 424/406 |
| 6,544,539 B1 * | 4/2003 | Ricketts | A01N 25/16 424/405 |
| 7,208,170 B2 | 4/2007 | Petersson | |
| 7,695,541 B1 | 4/2010 | Frizzell et al. | |
| 2003/0194415 A1 * | 10/2003 | Wang | A01N 33/24 424/400 |
| 2005/0238728 A1 * | 10/2005 | Evans | A61K 31/155 424/601 |
| 2011/0274770 A1 * | 11/2011 | Scholz | A01N 59/12 424/672 |
| 2016/0193232 A1 | 7/2016 | Beus et al. | |

FOREIGN PATENT DOCUMENTS

| | | |
|---|---|---|
| EP | 94219 | 11/1983 |
| EP | 473395 | 3/1992 |
| EP | 406275 | 5/1992 |
| EP | 1028736 | 4/2002 |

OTHER PUBLICATIONS

Anderson et al.; Am. J. Infect. Control; 2010; 38:826-31.*
Fox, LK, Colonization by *Staphylococcus aureus* on chapped teat skin: effect of iodine and chlorhexidine posmilking disinfectants, Journal of Dairy Science, Jan. 1992, pp. 66-71, vol. 75—Issue 1. (abstract only).
GEA Farm Technologies, The Dairy Farmer, Spring 2012, pp. 1-8.
Gleeson D et al., Effect of pre-milking teat preparation procedures on the microbial count on teats prior to cluster application, Irish Veterinary Journal, Jul. 2009, pp. 461-467, vol. 62—Issue 7.
Goodwin, PJ et al., Effectiveness of postmilking teat antisepsis with iodophor, chlorhexidine or dodecyl benzene sulphonic acid, Australian Society of Animal Production, 1996. (abstract only).
Nickerson, Stephen C., Choosing the Best Teat Dip for Mastitis Control and Milk Quality, NMC-PDPW Milk Quality Conference Proceedings, Apr. 2001, p. 43.

* cited by examiner

*Primary Examiner* — Jeffrey T. Palenik
(74) *Attorney, Agent, or Firm* — Clayton Howarth, P.C.

(57) ABSTRACT

An improved aqueous teat dip comprising iodine and chlorhexidine in an aqueous solution.

80 Claims, 1 Drawing Sheet

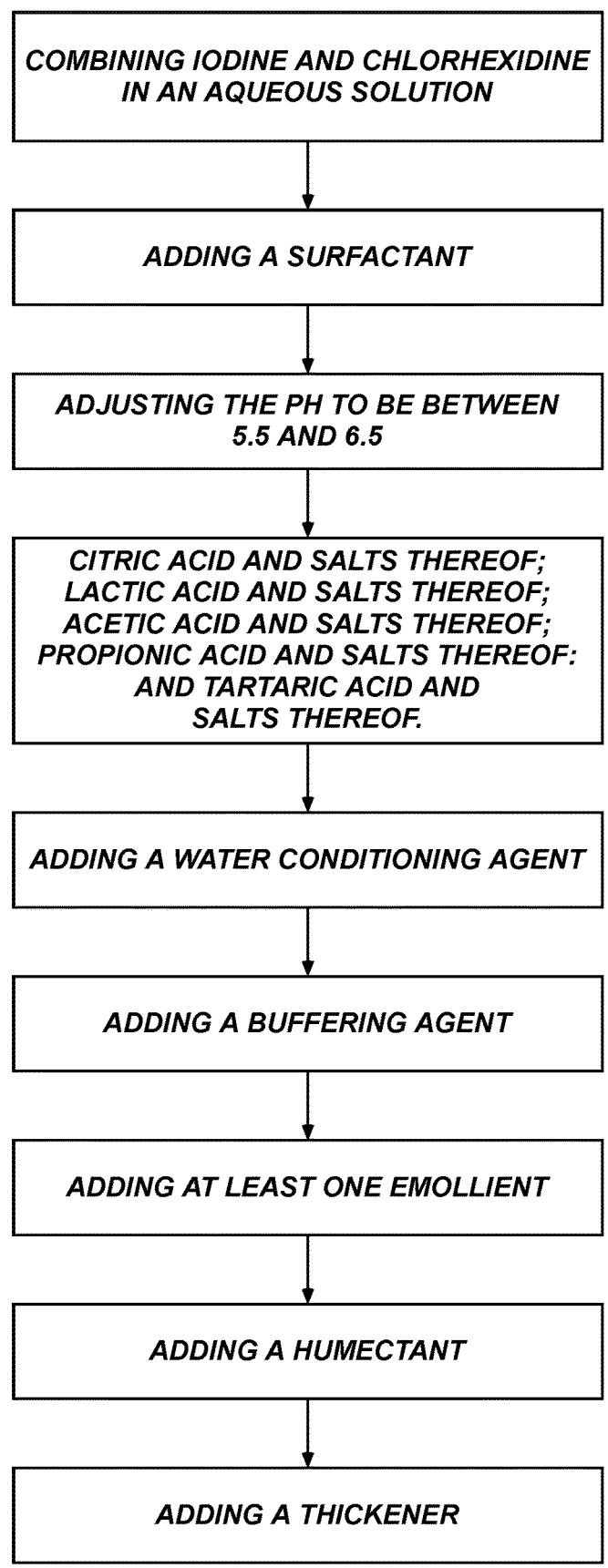

DAIRY ANIMAL TEAT DISINFECTANT

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND

1. The Field of the Present Disclosure

This disclosure is particularly directed towards an improved disinfectant. Specifically, this invention is directed towards the disinfection of the teat and udder skin of dairy animals.

2. Description of the Related Art

Infection of a dairy animal by microorganisms can result in mastitis—a bacterial infection which results in the loss of milk production, economic loss to the dairy farmer and in severe cases, death of the dairy animal. Modern methods of milking which utilize machines to draw milk from the animal's udder by applying a pulsating vacuum. These machines improve efficiency of the milking process by shortening the milking time and also enhance the cleanliness of the milk product. However, modern milking methods may also cause irritation and damage to the teat and udder of the dairy animal. Such irritation and damage may leave the animal more vulnerable to infection from available microorganisms such as the bacteria that cause mastitis.

These microorganisms may originate from the animal's skin, the hands of dairy workers, soil, water supplies and fecal matter from the animals themselves. Modern dairy practices, which often rely on the animals being kept in close proximity to each other, may increase the opportunity for infection. Mastitis infection is a threat to the well being of the dairy animal and a major economic problem for the dairy farmer. Mastitis is widely considered the single most costly disease in the industry. Thus, prevention of mastitis is a significant goal of the dairy farmer.

Dipping of the dairy animal's teats in an antimicrobial solution has been shown to be an effective method of reducing the incidence of mastitis. The antimicrobial dip can be applied after milking, before milking or both before and after milking. The important function of the teat dip is to prevent mastitis by killing or reducing the growth of disease causing microorganisms.

Ideally the teat dip product has broad spectrum antimicrobial activity and is formulated to prevent skin irritation. A variety of active ingredients are used in teat dips: sodium hypochlorite, chlorine dioxide, bromine, quaternary ammonium compounds, isocyanurate, chlorhexidine, iodine iodophors (iodine complexed with a detergent or polymer), detergents, and fatty acids are some of the ingredients currently in use. The various teat dips currently in use all have advantages combined with significant disadvantages. Some are unduly irritating, some have limited efficacy and some require extremes of pH. For example, iodophore iodine is among the most widely used active ingredients in teat dips. Iodine is a broad spectrum and fast acting antimicrobial disinfectant, but it can be irritating, has little residual effect and is expensive. In some circumstances, the addition of a surfactant helps to improve the effectiveness of the disinfectant.

Most of the above ingredients are used separately rather than in combination with other ingredients. For example, iodine is never encountered together with chlorhexidine in the known art. The combination of iodine and chlorhexidine has not been suggested or taught by the known art.

Thus, there continues to be a need in the dairy industry for a fast acting broad spectrum teat dip with improved characteristics.

BRIEF DESCRIPTION OF THE DRAWINGS

Reference will now be made to the accompanying drawing, wherein:

FIG. 1 is a flow chart illustrating a method of making a teat dip in accordance with the present disclosure.

DETAILED DESCRIPTION

For the purposes of promoting an understanding of the principles in accordance with the disclosure, reference will now be made to the embodiments described herein and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the present teat disinfectant is disclosed and described, it is to be understood that this disclosure is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present disclosure will be limited only by the appended claims and equivalents thereof.

It must be noted that, as used in this specification and the appended claims, the singular forms "a," "an," and "the" include plural referents unless the context clearly dictates otherwise.

In describing and claiming the present disclosure, the following terminology will be used in accordance with the definitions set out below.

As used herein, the terms "comprising," "including," "containing," "characterized by," and grammatical equivalents thereof are inclusive or open-ended terms that do not exclude additional, un-recited elements or method steps.

As used herein, the phrase "consisting of" and grammatical equivalents thereof exclude any element, step, or ingredient not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

This disclosure describes a topically applied aqueous composition with broad spectrum antimicrobial efficacy, rapid kill and residual antimicrobial efficacy. This disclosure further describes an aqueous teat dip composition comprised of two antimicrobial active ingredients such that one is iodine and one is chlorhexidine. It has been discovered that an antimicrobially effective aqueous teat dip formulation can be prepared in a stable and economic fashion by combining iodine and a chlorhexidine, most often a chlorhexidine salt, in the presence of non-ionic surfactants. Compositions of this invention may also contain buffering agents to regulate the formulation pH, water conditioning agents and additionally other teat dip ingredients known to those of ordinary skill in the art such as emollients, humectants, thickeners and colorant.

It is postulated that, without being bound by theory, the combination of these two antimicrobial active ingredients which act on different sites of the microorganisms will result in a broad spectrum antimicrobial formulation with some residual antimicrobial activity.

It is further postulated that the cell membrane permeabilizing effect of chlorhexidine will complement and augment action of iodine. It is further postulated that the well known ability of chlorhexidine to have residual antimicrobial effects when applied to skin will provide the formulations of this invention with an extended period of antimicrobial efficacy beyond the initial point of application.

Compositions of this invention may be prepared as ready to use teat dips or as concentrated preparations to be diluted for use. As used in this disclosure, concentrated form means any concentration wherein the water comprises no more than 60% by weight. Compositions of this invention are herein referred to as teat dips but it is understood that other methods of application are included such as spraying, foaming, or wiping as well as any application method that would be familiar to one of ordinary experience in the art.

In addition, it is understood that this disinfectant is intended for cows, goats or any other dairy animals but may also be useful as a general disinfectant or wound treatment.

Compositions of this disclosure have shown through testing excellent and rapidkill of gram negative organisms such as *Pseudomonas Aeruginosa, Klebsiella Pneumoniae, Serratia Marcescens*, and *Escherichia Coli* and gram positive organisms such as *Staphylococcus Aureus, Corynebacterium Bovis, Streptococcus Agalactiae, Streptococcus Dysagalactiae, Streptococcus Uberis* and the alga Prototheca Wickethamii.

The terms "weight percent," "percent by weight," and "% by weight" all refer to the concentration of a component substance as the weight of the component substance divided by the weight of the composition multiplied by 100. The weight percentages referred to herein shall be considered to include the ranges 1-2, 2-3, 1-3 and all the values within. Thus, if the weight percentage is 10, this would include the values 7 and 13 and all the values between those.

Reference will now be made to the specific embodiments of the described in the disclosure. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Iodine:

Compositions of the current disclosure shall include molecular iodine. An embodiment of the composition includes from 0.01 to 10 weight percent iodine. In another embodiment the composition includes from 0.1 to 5 weight percent iodine. Yet another embodiment includes from 0.2 to 2.5 weight percent iodine.

Iodine is a broad spectrum and fast acting germicide and antimicrobial disinfectant. It has limited residual effect and is expensive.

The source of iodine in this disclosure can be elemental iodine made soluble by the inclusion of an iodide salt such as potassium iodide or sodium iodide. Said iodide salt may range from 10 to 100 weight percent of the iodine, from 15 to 50 weight percent of the iodine used, or from 20 to 40 weight percent of the iodine used.

The source of iodine used in this disclosure may alternately be an iodophore (iodine complexed with a surfactant or a polymer). Acceptable iodophores for incorporation in the compositions of this disclosure can be constructed from any of the surfactants described in the current disclosure and other possibilities known to those of ordinary skill in the art. The source of iodine used in this disclosure may also be PVP iodine.

Chlorhexidine:

The source of chlorhexidine in the compositions of this disclosure can be any of the commercially available water soluble salts of chlorhexidine including but not limited to; chlorhexidine digluconate, chlorhexidine acetate, chlorhexidine hydrochloride, chlorhexidine lactate and chlorhexidine phosphate. Chlorhexidine comprises between 0.2% and 4% by weight.

Chlorhexidine is a longer acting germicide and antimicrobial disinfectant than iodine. Its combination with iodine in a teat dip provides for a longer acting and more effective teat dip.

Surfactants:

Non-ionic surfactants are a useful class of surfactants for use in this disclosure. Useful members of this class include nonylphenol ethoxylates, octylphenol ethoxylates, linear alcohol ethoxylates, branched alcohol ethoxylates, secondary alcohol ethoxylates, block copolymers of polyethylene oxide and polypropylene oxide, alkyl glucosides, alkyl polyglucosides, and alkylamine oxides. An embodiment of this invention includes 1 to weight percent non ionic surfactant. Another embodiment includes from 2 to 20 weight percent. Yet another embodiment includes from 3 to 15 weight percent surfactant.

pH Buffers:

Buffers useful for pH maintenance in this disclosure include citric acid and salts thereof, lactic acid and salts thereof, acetic acid and salts thereof, propionic acid and salts thereof and tartaric acid and salts thereof.

An embodiment of this disclosure includes from about 0.1 to about 4.0 weight percent buffering agent. Another embodiment of this disclosure includes from about 0.2 to about 2.0 weight percent buffering agent. Another embodiment of this disclosure includes from about 0.25 to about 1.0 weight percent buffering agent.

The pH of the current disclosure shall be maintained in an embodiment in the range of 2 to 10. In another embodiment the pH range is 4.5 to 7.5. In another embodiment the pH is from 5.5 to 6.5.

Water Conditioning Agents:

Water conditioning agents which are useful in this disclosure include citric acid and salts thereof, lactic acid and salts thereof, and phosphoric acid and salts thereof. An embodiment of this disclosure includes from 0.01 to 10 weight percent of water conditioning agent. Another embodiment includes from 1.0 to 5.0 weight percent water conditioning agent. Yet another embodiment includes from 0.25 to 2.0 weight percent water conditioning agent.

Emollients incorporated into the compositions of the present disclosure shall serve to assist the skin in retention of moisture. Useful emollients shall he compatible with the formulations of this disclosure. Some examples of useful emollients are lanolin, ethoxylated lanolin, polyols, fatty acid esters, and other materials as should be understood by those knowledgeable in the art. Suitable levels of incorporation of emollients in the present disclosure are from 0.1 to 50 weight percent, from 1.0 to 25 weight percent and from 2.0 to 5.0 weight percent. The emollients may be used to help counteract some of the drying and irritating effect of the active ingredients of the teat dip.

Humectants:

Humectants incorporated into the compositions of the present disclosure shall serve the purpose of drawing and holding moisture for the purpose of skin conditioning. Some useful humectants are glycerine, sorbitol, propylene glycol and other materials known to those of ordinary skill in the art. Suitable humectant levels of incorporation in the present disclosure are from 0.1 to 20 weight percent from 0.5 to 15 weight percent and from 1.0 to 10 weight percent.

Thickeners:

Thickeners can be used to control the rheology of the formulations of the present disclosure. Useful thickeners need be compatible with the formulations of this disclosure include gums, cationic gums and others familiar to one of ordinary skill in the art.

Colorants:

Colorants may optionally be included in the formulations of the present disclosure and must be GRAS (Generally Recognized As Safe) for food. Useful colorants include dyes, pigments and carmel coloring. An embodiment includes approximately 0.03 weight percent or less colorant by weight, approximately 0.01 weight percent or less, or approximately 0.005 weight percent or less.

EXAMPLES

The following examples are set forth in Table A and are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.) but some errors and deviations should be accounted for. Unless indicated otherwise indicated, parts are parts by weight, temperature is in degrees Celsius, or is at ambient temperature, and pressure is at or near on atmosphere. The following table contains several embodiments for exemplary purposes. It will be understood that no limitation of the scope of the disclosure is intended by these. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

TABLE A

| Ingredient | Example 1 | Example 2 | Example 3 | Example 4 | Example 5 | Example 6 | Example 7 | Example 8 |
| --- | --- | --- | --- | --- | --- | --- | --- | --- |
| Water | 79.3 | 86.4 | 74.46 | 87.122 | 88.92 | 85 | 80 | 90 |
| Iodophore (20% by wt. Iodine) | 2.8 | 2.8 | 5.6 | 1.36 | 0.0 | 7 | 5 | 0.5 |
| Glycerin | 4.0 | 2.0 | 4.0 | 4.0 | 2.0 | 0.0 | 0.0 | 0.0 |
| Citric acid | .05 | .05 | .10 | .05 | .05 | 0.0 | 0.0 | 0.0 |
| Sod. citrate | .45 | .45 | .9 | .45 | .45 | 0.0 | 0.0 | 0.0 |
| Pot. Iodide | 0.0 | 0.0 | 0.0 | .09 | .2 | 0.0 | 0.0 | 0.0 |
| Pot. Iodate | .1 | .1 | .14 | .118 | .08 | 0.0 | 0.0 | 0.0 |
| Co 887 nonionic surfactant | 0.0 | 0.0 | 0.0 | 1.5 | 0.0 | 0.0 | 0.0 | 0.0 |
| Block copolymer Pluronic 104 | 0.0 | 0.0 | 0.0 | 0.0 | 5.0 | 0.0 | 0.0 | 0.0 |
| Elemental Iodine | 0.0 | 0.0 | 0.0 | 0.0 | .50 | 0.0 | 0.0 | 0.0 |
| 12 mole nonyl phenol ethoxylate nonionic surfactant | 10.5 | 5.1 | 12.0 | 2.5 | 0.0 | 0.0 | 12 | 9 |
| Chlorhexidine gluconate (20% by wt. Chlorhexidine) | 2.8 | 2.8 | 2.8 | 2.8 | 2.8 | 8 | 3 | 0.5 |
| FD+C yellow #5 | 0.0 | 0.0 | 0.0 | .01 | 0.0 | 0.0 | 0.0 | 0.0 |

Example 1

Example 1 is predicted to be at least as effective as Example 2, possessing active ingredients in the same proportions as the mixture of example 2. The mixture of Example 1 differs from the mixture of Example 2 only with regard to having a lower percentage of water and a higher percentage of surfactant. Hence, the mixture of Example 1 is postulated to be very effective.

Example 2

Example 2 was tested in vitro via a modified AOAC protocol and found to be very effective, being equivalent to a commercial 1.0% Iodine teat dip at 15 seconds, 30 seconds and 45 seconds exposure time vs. Prototheca *Wickerhamii* ATCC 16529, *Streptococcus Uberis* 15442, *Staphylococcus Aureus* ATCC 25923, *Serratia Marcescens* ATCC 14756, *Corynebacterium Bovis* ATCC 7715, *Streptococcus Agalactiae* ATCC 27956, *Streptococcus Dysgalactiae* ATCC 43078, *Escherichia Coli* ATCC 25922.

Example 3

Example 3 is predicted to be more effective than the mixture of Example 2. Example 3 possesses iodine compounds in greater concentrations than the mixture of Example 2 and chlorhexidine in concentrations equal to that of Example 2. Hence, the mixture of Example 3 is postulated to be very effective.

Example 4

Example 4 is predicted to be less effective than the mixture of Example 2. Example 4 possesses iodine compounds in lesser concentrations than the mixture of Example 2 and chlorhexidine in concentrations equal to that of Example 2. Hence, the mixture of Example 4 is postulated to be fairly effective.

Example 5

Example 5 has 0.5% Iodine added as elemental iodine. This is about the same concentration of iodine as in examples 1 and 2. Thus, Example 5 is predicted to be about as effective as Examples 1 or 2. Example 5 possesses iodine compounds in lesser concentrations than either the mixture of Example 2 or Example 4. Hence, the mixture of Example 5 is postulated to be somewhat effective.

Example 6

Example 6 is comprised of 85% water, 7% iodophore and 8% chlorhexidine gluconate. It is predicted to be somewhat effective.

Example 7

Example 7 is comprised 80% water, 5% iodophore, 12% 12 mole nonyl phenol ethoxylate nonionic surfactant and 3% chlorhexidine gluconate. It is predicted to be somewhat effective.

Example 8

Example 8 is comprised of 90% water, 0.5% iodophore, 9% 12 mole nonyl phenol ethoxylate nonionic surfactant and 0.5% chlorhexidine gluconate. It is predicted to be ineffective.

In accordance with the present disclosure, one representative method of making an embodiment falling within the scope of the present disclosure is represented in FIG. 1. In FIG. 1, the step of combining iodine and chlorhexidine in an aqueous solution is described. An additional optional step of adding a surfactant is also described. A further step of adjusting the pH to be between about 5.5 and about 6.5 is shown. An additional optional step of adding citric acid and salts thereof is illustrated. An additional optional step of adding lactic acid and salts thereof is described. Further optional steps of adding acetic acid and salts thereof, adding propionic acid and salts thereof, adding tartaric acid and salts thereof, adding a water conditioning agent, adding a buffering agent, adding at least one emollient, adding a humectant and adding a thickener are all disclosed.

In view of the foregoing, it will be appreciated that the present disclosure provides a teat disinfectant which provides advantages and benefits not previously available. In particular, the beneficial combination of iodine and chlorhexidine produces results in terms of its ability to kill microbes as well as its extended duration of effectiveness which is not know in the industry and which would be unexpected by those of ordinary skill in the pertinent art.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of any single foregoing disclosed embodiment. Thus, the following claims are hereby incorporated into this Detailed Description by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in quantities, proportions, materials, and manner of making and use may be made without departing from the principles and concepts set forth herein.

What is claimed is:

1. A teat dip comprising;
   iodine, comprising a mixture of an iodide salt and an iodophore, said iodide salt is sodium iodide and wherein the iodine comprises about 0.1 to about 5 weight percent of the teat dip, said iodide salt comprises from about 10% to 100% of said iodine and said iodophore comprises the remaining iodine; and
   a Chlorhexidine salt selected from Chlorhexidine hydrochloride, Chlorhexidine lactate, or Chlorhexidine phosphate, where the Chlorhexidine salt further comprises between 0.2% and 4% of the composition by weight.

2. The teat dip of claim 1 further comprising a surfactant.

3. The teat dip of claim 2 wherein the surfactant is selected from octylphenol ethoxylates; branched alcohol ethoxylates, secondary alcohol ethoxylates; block copolymers of polyethylene oxide and polypropylene oxide; alkyl glucosides; alkyl polyglucosides, and alkylamine oxides.

4. The teat dip of claim 2 wherein the surfactant is non ionic.

5. The teat dip of claim of 4 wherein the surfactant comprises from about 3 from about 15 weight percent.

6. The teat dip of claim 1 having a pH of between 4.5 and 7.5.

7. The teat dip of claim 1 having a pH of between 5.5 and 6.5.

8. The teat dip of claim 1 further comprising a water conditioning agent.

9. The teat dip of claim 8 wherein the water conditioning agent is selected from citric acid and salts thereof; lactic acid and salts thereof; and phosphoric acid and salts thereof.

10. The teat dip of claim 1, further comprising at least one buffering agent.

11. The teat dip of claim 1, further comprising at least on emollient.

12. The teat dip of claim 1 further comprising a humectant.

13. The teat dip of claim 12 wherein the humectant is selected from glycerine; sorbitol; and propylene glycol.

14. The teat dip of claim 13 wherein the humectant comprises from about 0.5 from about 15 weight percent.

15. The teat dip of claim 1 further comprising at least one thickener.

16. The teat dip of claim 1 further comprising at least one colorant.

17. The teat dip of claim 1 wherein the iodine further comprises elemental iodine.

18. The teat dip of claim 1 wherein the teat dip is an aqueous teat dip.

19. The teat dip of claim 1 wherein the teat dip is in a concentrated form.

20. An aqueous teat dip comprising;
   iodine, comprising a mixture of an iodide salt and an iodophore, said iodide salt is sodium iodide and wherein the iodine comprises about 0.1 to about 5 weight percent of the teat dip, said iodide salt comprises from about 10% to 100% of said iodine and said iodophore comprises the remaining iodine; and
   a Chlorhexidine salt selected from Chlorhexidine hydrochloride, Chlorhexidine lactate, or Chlorhexidine phosphate, where the Chlorhexidine salt further comprises between 0.2% and 4% of the composition by weight;
   a surfactant selected from octylphenol ethoxylates, branched alcohol ethoxylates, secondary alcohol ethoxylates, block copolymers of polyethylene oxide and polypropylene oxide, alkyl glucosides, alkyl polyglucosides, and alkylamine oxides.

21. The aqueous teat dip of claim 20 wherein the surfactant comprises between about 1% and about 20% by weight.

22. The aqueous teat dip of claim 20 claim having a pH of between about 4.5 and about 7.5.

23. The aqueous teat dip of claim 20 having a pH of between about 4 and about 10.

24. The aqueous teat dip of claim 20 having a pH of between about 5.5 and about 6.5.

25. The aqueous teat dip of claim 24 wherein the teat dip is in a concentrated form.

26. The aqueous teat dip of claim 20 further comprising a pH buffer.

27. The aqueous teat dip of claim 26 wherein the pH buffer is selected from citric acid and salts thereof; lactic acid and salts thereof; acetic acid and salts thereof; propionic acid and salts thereof; and tartaric acid and salts thereof.

28. The aqueous teat dip of claim 20 further comprising a water conditioning agent.

29. The aqueous teat dip of claim 28 wherein the water conditioning agent is selected from citric acid and salts thereof; lactic acid and salts thereof; and phosphoric acid and salts thereof.

30. The aqueous teat dip of claim 28 wherein the water conditioning agent comprises between about 0.01 and about 10 weight percent of a water conditioning agent.

31. The aqueous teat dip of claim 28 wherein the water conditioning agent comprises from about 1.0 from about 5.0 weight percent.

32. The aqueous teat dip of claim 28 wherein the water conditioning agent comprises from about 0.25 from about 2.0 weight percent.

33. The aqueous teat dip of claim 20 wherein the surfactant comprises from about 1 to about 50 weight percent.

34. The aqueous teat dip of claim of 20 wherein the surfactant comprises from about 3 to about 15 weight percent.

35. The aqueous teat dip of claim 20, further comprising at least one buffering agent.

36. The aqueous teat dip of claim 20, further comprising at least one water conditioning agent.

37. The aqueous teat dip of claim 36 wherein the water conditioning agent is from about 1.0% from about 5.0% by weight.

38. The aqueous teat dip of claim 20 wherein the surfactant comprises between 1% and 20% by weight.

39. The aqueous teat dip of claim 20, further comprising at least one emollient.

40. The aqueous teat dip of claim 20 further comprising a humectant.

41. The aqueous teat dip of claim 40 wherein the humectant is selected from glycerine; sorbitol; and propylene glycol.

42. The aqueous teat dip of claim 40 wherein the humectant comprises from about 0.1 from about 20 weight percent.

43. The aqueous teat dip of claim 40 wherein the humectant comprises from about 0.5 from about 15 weight percent.

44. The aqueous teat dip of claim 40 wherein the humectant comprises from about 1.0 from about 10 weight percent.

45. The aqueous teat dip of claim 20 further comprising at least one thickener.

46. The aqueous teat dip of claim 20 further comprising at least one colorant.

47. The aqueous teat dip of claim 20 wherein the iodine further comprises elemental iodine.

48. The aqueous teat dip of claim 20 wherein the iodine further comprises between about 0.2% and about 2.5% by weight.

49. The aqueous teat dip of claim 20 claim having a pH of between about 4.5 and about 7.5.

50. The aqueous teat dip of claim 20 having a pH of between about 4 and about 10.

51. The aqueous teat dip of claim 20 having a pH of between about 5.5 and about 6.5.

52. An aqueous teat dip comprising:
   iodine, comprising a mixture of an iodide salt and an iodophore, said iodide salt selected from potassium iodide or sodium iodide, and said iodine comprising between about 0.2% and about 2.5% by weight of the teat dip;
   a chlorhexidine salt selected from chlorhexidine hydrochloride, chlorhexidine lactate, or chlorhexidine phosphate, said chlorhexidine salt comprising between about 0.2% and about 4% by weight of the teat dip;
   a surfactant selected from octylphenol ethoxylates; branched alcohol ethoxylates; secondary alcohol ethoxylates; block copolymers of polyethylene oxide and polypropylene oxide; alkyl glucosides; alkyl polyglucosides; and alkylamine oxides;

a humectant comprising propylene glycol;

a water conditioning agent selected from lactic acid and salts thereof;

a thickener; and a colorant;

wherein the teat dip has a pH of between about 5.5 and about 6.5.

53. A method for preparing an aqueous teat dip comprising the step of combining:

iodine, comprising a mixture of an iodide salt and an iodophore, said iodide salt is sodium iodide and wherein the iodine is added in sufficient quantities to comprise about 0.1 to about 5 weight percent of the teat dip, said iodide salt comprising from about 10% to 100% of said iodine and said iodophore comprising the remaining iodine; and a Chlorhexidine salt selected from Chlorhexidine hydrochloride, Chlorhexidine lactate, or Chlorhexidine phosphate, where the Chlorhexidine salt is added in sufficient quantities to comprise between 0.2% and 4% by weight of the teat dip.

54. The method of claim 53 further including the step of adding a surfactant to the teat dip.

55. The method of claim 54 wherein the surfactant is added in sufficient quantity that the surfactant comprises between about 1% and about 20% by weight.

56. The method of claim 54 further comprising the step of adjusting the pH of the aqueous teat dip to a pH of between about 4.5 and about 7.5.

57. The method of claim 54 further comprising the step of adjusting the pH of the aqueous teat dip to a pH of between about 4 and about 10.

58. The method of claim 54 further comprising the aqueous teat dip of claim 54 having a pH of between about 5.5 and about 6.5.

59. The method of claim 54 further comprising the step of adding a pH buffer.

60. The method of claim 54 further comprising the step of selecting the pH buffer from citric acid and salts thereof; lactic acid and salts thereof; acetic acid and salts thereof; propionic acid and salts thereof; and tartaric acid and salts thereof.

61. The method of claim 54 further comprising the step of adding a water conditioning agent.

62. The method of claim 61 wherein the water conditioning agent is selected from citric acid and salts thereof; lactic acid and salts thereof; and phosphoric acid and salts thereof.

63. The method of claim 61 wherein the water conditioning agent is added in sufficient quantity so as to comprises between about 0.01 to about 10 weight percent.

64. The method of claim 61 wherein the water conditioning agent is added in sufficient quantity so as to comprise between about 1.0 to about 5.0 weight percent.

65. The method of claim 61 wherein the water conditioning agent is added in sufficient quantity so as to comprise between about 0.25 to about 2.0 weight percent.

66. The method of claim 54 wherein the surfactant is selected from octylphenol ethoxylates; branched alcohol ethoxylates; secondary alcohol ethoxylates; block copolymers of polyethylene oxide and polypropylene oxide; alkyl glucosides; alkyl polyglucosides; and alkylamine oxides.

67. The method of claim 54 wherein the added surfactant is non ionic.

68. The method of claim 54 wherein the surfactant is added in sufficient quantity such that it comprises about 1 to about 50 weight percent.

69. The method of claim 54 wherein the surfactant is added in sufficient quantity such that it comprises about 3 to about 15 weight percent.

70. The method of claim 54 further comprising the step of adding a buffering agent.

71. The method of claim 54 further comprising the step of adding at least one emollient.

72. The method of claim 54 further comprising the step of adding a humectant.

73. The method of claim 72 wherein the humectant is selected from glycerine; sorbitol; and propylene glycol.

74. The method of claim 73 wherein the humectant is added in sufficient quantities such that it comprises from about 1.0 to about 10 weight percent.

75. The method of claim 72 wherein the humectant is added in sufficient quantities such that it comprises from about 0.1 to about 20 weight percent.

76. The method of claim 72 wherein the humectant is added in sufficient quantities such that it comprises from about 0.5 to about 15 weight percent.

77. The method of claim 54 further comprising the step of adding at least one thickener.

78. The method of claim 54 wherein the iodine further comprises elemental iodine.

79. The method of claim 54 wherein the iodine is added in sufficient quantities so as to further comprise between about 0.2% and about 2.5% by weight.

80. A method of treating a dairy animal's teats by applying the mixture of claim 54 to a dairy animal's teats.

* * * * *